US00PP17557P2

(12) United States Plant Patent
Retkes

(10) Patent No.: US PP17,557 P2
(45) Date of Patent: Apr. 3, 2007

(54) ***OXALIS* PLANT NAMED 'JROXBURWI'**

(50) Latin Name: *Oxalis regnellii*
Varietal Denomination: Jroxburwi

(76) Inventor: Jósef Retkes, Szent Impre h. u12/A, H-9700, Szombathely (HU)

( * ) Notice: Subject to any disclaimer, the term of this patent is extended or adjusted under 35 U.S.C. 154(b) by 0 days.

(21) Appl. No.: 11/236,744

(22) Filed: Sep. 27, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Oxalis* plant named 'Jroxburwi', characterized by its upright, outwardly spreading and uniformly mounded plant habit; numerous basal leaves; dense and bushy plant form; freely flowering habit; dark purple-colored foliage; and white-colored flowers.

1 Drawing Sheet

Botanical designation: *Oxalis regnellii.*
Cultivar denomination: 'Jroxburwi'.

BACKGROUND OF THE INVENTION

The present Invention relates to a new and distinct cultivar of *Oxalis* plant, botanically known as *Oxalis regnellii,* and hereinafter referred to by the cultivar name 'Jroxburwi'.

The new *Oxalis* is a product of a planned breeding program conducted by the Inventor in Szombathely, Hungary. The objective of the program is to create new *Oxalis* cultivars with attractive foliage and flower colors.

The new *Oxalis* originated from a cross-pollination made by the Inventor in 1993 of two unnamed selections of *Oxalis regnellii,* not patented. The new *Oxalis* was discovered and selected from the resultant progeny of the stated cross-pollination by the Inventor in a controlled environment in Szombathely, Hungary in 2001.

Asexual reproduction of the new cultivar by terminal cuttings in a controlled environment in Szombathely, Hungary since the summer of 2002, has shown that the unique features of this new *Oxalis* are stable and reproduced true to type in successive generations.

SUMMARY OF THE INVENTION

Plants of the cultivar Jroxburwi have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Jroxburwi'. These characteristics in combination distinguish 'Jroxburwi' as a new and distinct cultivar of *Oxalis.*

1. Upright, outwardly spreading and uniformly mounded plant habit.
2. Numerous basal leaves; dense and bushy plant form.
3. Freely flowering habit.
4. Dark purple-colored foliage.
5. White-colored flowers.

Plants of the new *Oxalis* differ primarily from plants of the parent selections in the following characteristics:

1. Plants of the new *Oxalis* have dark purple-colored foliage whereas plants of the parent selections have green-colored foliage.
2. Plants of the new *Oxalis* are more freely flowering than plants of the parent selections.

Plants of the new *Oxalis* can be compared to plants of the cultivar Deep Purple, not patented. In side-by-side comparisons conducted in Southern California, plants of the new *Oxalis* differed from plants of the cultivar Deep Purple primarily in leaf color as plants of the cultivar Deep Purple had red purple-colored leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Oxalis.*

The photograph at the top of the sheet is a close-up view of typical flowers and leaves of 'Jroxburwi'.

The photograph at the bottom of the sheet comprises a side perspective view of a typical plant of 'Jroxburwi' grown in a container.

DETAILED BOTANICAL DESCRIPTION

In the following description, color references are made to The Royal Horticultural Society Colour Chart, 1995 Edition, except where general terms of ordinary dictionary significance are used. Plants grown in one gallon were used for the aforementioned photographs and following description. Plants were about 16 weeks from planting rooted cuttings. Plants were grown under conditions which closely approximate commercial production conditions during the spring in Bonsall, Calif. in a polyethylene-covered greenhouse. During the production period, day temperatures ranged from 13°

C. to 35° C. and night temperatures ranged from 13° C. to 21° C.

Botanical classification: *Oxalis regnellii* cultivar Jroxburwi.

Parentage:

*Female, or seed, parent.*—Unnamed selection of *Oxalis regnellii,* not patented.

*Male, or pollen, parent.*—Unnamed selection of *Oxalis regnellii,* not patented.

Propagation:

*Type cutting.*—By divisions.

*Time to produce a rooted young plant.*—About 20 days at 20° C.

*Root description.*—Fine, freely-branching; whitish in color.

*Rhizome description.*—Length: About 2 cm. Diameter: About 1.5 cm. Scale length: About 7 mm. Scale width: About 9 mm. Texture: Smooth, glabrous; scaly. Color: Close to 155A overlain with 30C.

Plant description:

*Form.*—Herbaceous perennial flowering plant; upright, outwardly spreading and uniformly mounded plant habit.

*Plant height.*—About 23 cm.

*Plant diameter.*—About 38 cm.

*Growth rate.*—Moderate to rapid growth rate; vigorous.

*Foliage description.*—Arrangement: Arising from rhizomes, basal; clover like, palmate three-foliate; about ten to twelve leaves per rhizome. Leaf length: About 6.4 cm. Leaf width: About 6.4 cm. Leaflet length: About 4.2 cm. Leaflet width: About 6.4 cm. Leaflet shape: Broadly obtriangular. Leaflet apex: Emarginate. Base: Attenuate. Margin: Entire. Texture, upper and lower surfaces: Smooth, glabrous. Venation pattern: Pinnate; reticulate. Color: Developing foliage, upper surface: 182A. Developing foliage, lower surface: 184B. Fully expanded foliage, upper surface: 79A. Fully expanded foliage, lower surface: 187A. Venation, upper surface: 79A. Venation, lower surface: 187B. Petiole: Length: About 19.8 cm. Diameter: About 2 mm. Texture, upper and lower surfaces: Smooth, glabrous. Color, upper and lower surfaces: 144A.

Flower description:

*Flower type and habit.*—Rotate single flowers single, scapose and arranged in umbels. Flowers facing upright or outwardly and positioned just at or slightly below the foliage. Flowers not persistent. Freely flowering habit, about eight flowers per umbel. Flowers not fragrant.

*Natural flowering season.*—Year-round in Southern California; flowering continuous during this period.

*Time to flower.*—Early flowering; plants begin flowering about four weeks after planting.

*Flower longevity on the plant.*—About five days.

*Inflorescence length.*—About 5 cm.

*Inflorescence diameter.*—About 4.5 cm.

*Flower diameter.*—About 2.5 cm.

*Flower depth.*—About 1.5 cm.

*Flower buds.*—Length: About 1 cm. Diameter: About 3 mm. Shape: Elongated oblong. Color: 157B.

*Corolla.*—Arrangement/appearance: Single whorl of five petals, fused into flared trumpet. Petal length from throat: About 2.2 cm. Petal width: About 8 mm. Petal shape: Obovate. Petal apex: Rounded. Petal margin: Entire. Petal texture, upper and lower surfaces: Smooth, glabrous; satiny. Color: Petal, when opening, upper surface: 155B. Petal, when opening, lower surface: 155A. Petal, opened flower, upper surface: 155D; towards the base, 144B. Petal, opened flower, lower surface: 155B.

*Sepals.*—Arrangement/appearance: Single whorl of five sepals, fused at base into a slender tube. Length: About 6 mm. Width: About 2 mm. Shape: Lanceolate. Apex: Acute. Margin: Entire. Texture, upper and lower surfaces: Pubescent. Color, upper and lower surfaces: 144A.

*Peduncles.*—Length: About 21 cm. Width: About 2 mm. Strength: Moderately strong. Angle: Mostly erect. Texture: Smooth, glabrous. Color: 144B.

*Pedicels.*—Length: About 3 cm. Width: About 1 mm. Strength: Moderately strong. Angle: About 30° to 45° from vertical. Texture: Smooth, glabrous. Color: 144A.

*Reproductive organs.*—Stamens: Quantity: About ten in two whorls. Anther shape: Oval. Anther length: Less than 1 mm. Anther color: 8A. Pollen amount: Scarce. Pollen color: 8A. Pistils: Quantity: One per flower. Pistil length: About 7 mm. Stigma shape: Round. Stigma color: 146B. Style length: About 5 mm. Style color: 145B. Ovary color: 145B.

*Seed/fruit.*—Seed and fruit production has not been observed.

Disease/pest resistance: Plants of the new *Oxalis* have not been noted to be resistant to other pathogens and pests common to *Oxalis.*

Weather/temperature tolerance: Plants of the new *Oxalis* are tolerant to rain and wind and have been observed to tolerate temperatures from −2° C. to 40° C.

It is claimed:

1. A new and distinct cultivar of *Oxalis* plant named 'Jroxburwi', as illustrated and described.

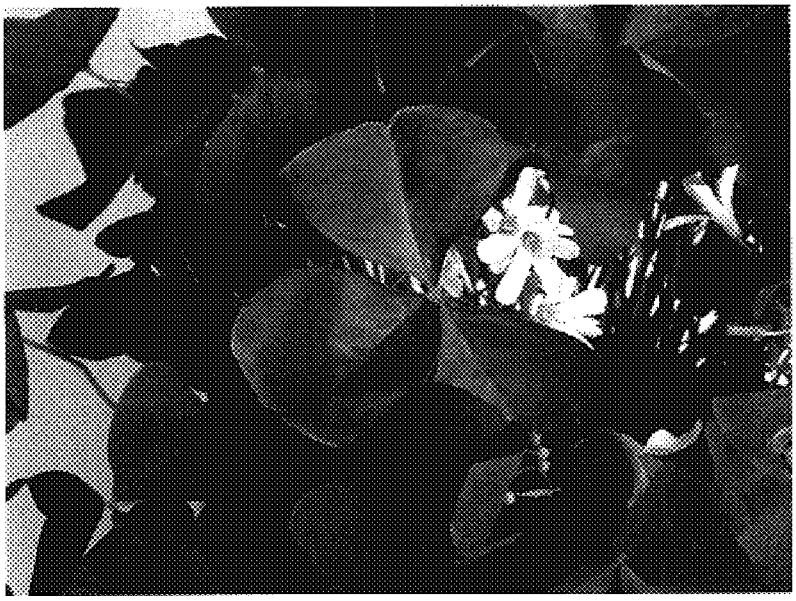
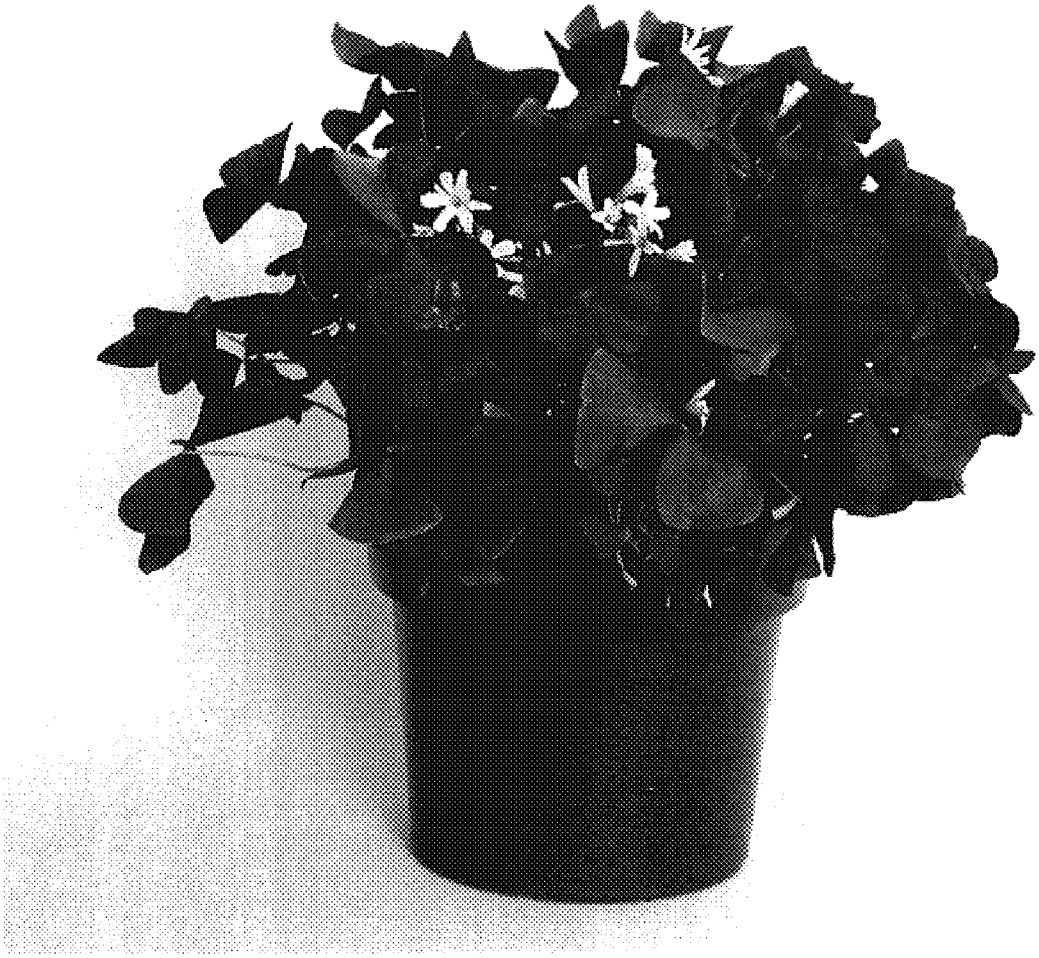

* * * * *